United States Patent [19]
Lindsay

[11] Patent Number: 6,123,818
[45] Date of Patent: Sep. 26, 2000

[54] GAS DETECTING APPARATUS HAVING CONDITION MONITORING MEANS

[75] Inventor: John Lindsay, Wimbourne, United Kingdom

[73] Assignee: Zellweger Analytics Ltd., Dorset, United Kingdom

[21] Appl. No.: 08/959,328

[22] Filed: Oct. 28, 1997

[30] Foreign Application Priority Data

Oct. 29, 1996 [EP] European Pat. Off. .............. 96307819

[51] Int. Cl.$^7$ .................................................. G01N 27/26
[52] U.S. Cl. ........................................ 204/400; 204/406
[58] Field of Search .................................. 204/400, 406, 204/401; 324/133, 500, 522, 527

[56] References Cited

U.S. PATENT DOCUMENTS

| | | | |
|---|---|---|---|
| 3,661,748 | 5/1972 | Blackmer | 204/401 |
| 3,718,568 | 2/1973 | Neuwelt | 204/401 |
| 4,088,986 | 5/1978 | Boucher . | |
| 4,868,508 | 9/1989 | Ohishi | 324/525 |
| 5,202,637 | 4/1993 | Jones | 324/425 |

FOREIGN PATENT DOCUMENTS

| | | |
|---|---|---|
| 0039549 | 11/1981 | European Pat. Off. . |
| 0241601 | 10/1987 | European Pat. Off. . |
| 0508966 | 10/1992 | European Pat. Off. . |
| 4318891 | 12/1994 | Germany . |
| 19510574 | 6/1996 | Germany . |
| 60-63473 | 4/1985 | Japan . |
| 1-44843 | 2/1989 | Japan . |
| 1-242958 | 9/1989 | Japan . |
| 636447 | 5/1983 | Switzerland . |
| WO90/12315 | 10/1990 | WIPO . |

*Primary Examiner*—Robert J. Warden, Sr.
*Assistant Examiner*—Andrew Aldag
*Attorney, Agent, or Firm*—Dilworth & Barrese

[57] ABSTRACT

An operational amplifier (34) has its inverting input connected to a electrochemical gas sensor (38) for amplifying the current produced thereby in response to presence of a predetermined gas. In order to determine whether a sensor (38) is indeed present and that a sensor present is serviceable, a transient is applied to the non-inverting input of the operation amplifier (34). The presence or absence of the sensor (38) alters the transfer function of the operational amplifier (34) in respect of the test signal. If a serviceable sensor (38) is present, the gain of the operational amplifier (34) is high for the transient resulting at square pulse output. However, if a serviceable sensor (38) is not present, the gain of the operational amplifier (34) is relatively low and the transient retains its original form. Consequently the presence of a serviceable sensor (38) can be determined from the output of the operational amplifier (34) in response to the transient test signal.

14 Claims, 5 Drawing Sheets

GAS DETECTING APPARATUS HAVING CONDITION MONITORING MEANS

FIELD OF THE INVENTION

The present invention relates to self-testing gas detecting apparatus.

BACKGROUND TO THE INVENTION

Electrochemical gas sensors typically comprise two or three electrodes separated by an electrolyte. These sensors generate currents in response to the presence of a gas, e.g. carbon monoxide hydrogen sulphide, sulphur dioxide, ammonia, for which they are adapted. Hitherto, faults in such sensors, for example broken signal wires or loss of electrolyte, have been detected by applying a quantity of the gas to be detected to a sensor while monitoring the sensor output. If a wire is broken or the electrolyte has leaked away, there will be no, or at least a reduced, output current.

The need to test such sensors by applying quantities of gas has a number of disadvantages. Staff are required to visit each sensor which is time consuming and undesirable if a sensor is located in a clean environment such as is found in semiconductor processing plants. Also, if a sensor fails, its failure will not be detected until the next test. This of course is undesirable where the sensor is used to detect a toxic gas or explosive. Furthermore, if the gas to be detected is toxic, it is undesirable that it be deliberately released during the testing process and for domestic use, in particular, this method of testing is quite unsuitable.

SUMMARY OF THE INVENTION

It is an aim of the present invention to overcome the aforementioned problems.

Broadly stated, the present invention provides a gas detecting apparatus including connection means for providing electrical connection to an electrochemical gas sensor, test means for generating a test signal and means to analyse a signal derived from the test signal to determine whether a serviceable electrochemical gas sensor is connected to the connection means.

A class of gas detecting apparatus to which the present invention is applicable comprise an amplifier and connection means for connecting an electrochemical gas sensor to the amplifier such that the amplifier is operable to amplify the output of the sensor.

According to a first aspect of the present invention, there is provided A self-testing gas detecting apparatus comprising an electrical interconnection for making a connection to an electrochemical gas sensor, a test signal generating circuit for generating a test signal, an amplifier for processing the test signal from the test signal generating circuit according to a transfer function, and a signalling device, said interconnection being arranged for connecting an electrochemical gas sensor as a component of the amplifier so as to determine said transfer function, wherein the signalling device is responsive to the processed test signal output by the amplifier to signal a fault condition if the processed test signal is not indicative of a serviceable electrochemical gas sensor being connnected into the amplifying circuit by said interconnection.

According to a second aspect of the present invention, there is provided a gas detecting apparatus comprising an electrical interconnection for receiving a two-terminal electrochemical gas sensor, a test signal generating circuit for generating a test signal, an amplifier for processing a test signal from the test signal generating circuit and processing means responsive to the processed test signal output by the amplifier to determine whether a serviceable electrochemical gas sensor is connected to the interconnection, the interconnection being arranged for connecting an electrochemical gas sensor to the amplifier such that the transfer function of the amplifier for the test signal is influenced thereby.

The interconnection preferably comprises a socket. However, the interconnection may comprise means to which a sensor may be conveniently soldered. The physical nature of the interconnection is not critical to the present invention, the key feature being the electrical relationship between the sensor and the amplifier. It should be noted that the test signal is not applied directly to the sensor and the result analysed. Instead, the presence of a serviceable sensor is determined indirectly from the output of the amplifier produced in response to the test signal.

Since, the transfer function of the amplifier for the test signal is influenced by the presence or absence of a serviceable electrochemical gas sensor, the output of the amplifier, in response to the test signal, will vary depending on the presence or absence of a serviceable gas sensor. The transfer function may be modified in respect of the amplifier's gain for the test signal or the phase shift introduced into the test signal by the amplifier. Preferably, however, the interconnection is configured such that the presence of a serviceable electrochemical cell increases the gain of the amplifier for said test signal.

If the test means is configured such that the test signal causes the amplifier to give a large output or saturate when a serviceable electrochemical sensor is connected to the amplifier by the interconnection, it is relatively simple to detect the presence of a sensor, for example using a digital or analogue comparator. A threshold for electrolyte loss can be set by testing the level of the amplifier output at a predetermined period after the start of the test signal. This is because the lower levels of electrolyte will result in the output of the amplifier being above the predetermined threshold for shorter periods.

Preferably, the amplifier is an operational amplifier, the interconnection is configured for connecting an electrochemical cell between the inverting input of the operational amplifier and earth, and the test means is configured to apply the test signal to the non-inverting input of the operational amplifier.

Conveniently, the test signal comprises a transient. The transient may be generated by means to produce a voltage step and differentiator for differentiating the voltage step to produce the test signal. The voltage step may be produced by a potential divider coupled between the amplifier's power supply lines. Thus, the sensor will be tested each time the amplifier is energised. However, a transient or ac signal may be applied at any time. Application of an ac signal at an appropriate frequency will result in the amplifier outputting a series of pulses.

In battery operated apparatus, power consumption is often reduced by intermittently operating circuits. Test signal generation linked to energising of the amplifier is particularly suited to such apparatus. Advantageously, therefore, apparatus according to the present invention includes control means and switching means for switching the supply of power to the amplifier and the test means, wherein the control means is operable to cyclically energise the amplifier and the test means.

DESCRIPTION OF PREFERRED EMBODIMENT

A preferred embodiment of the present invention will now be described, by way of example, with reference to the accompanying drawings.

Figure 1:
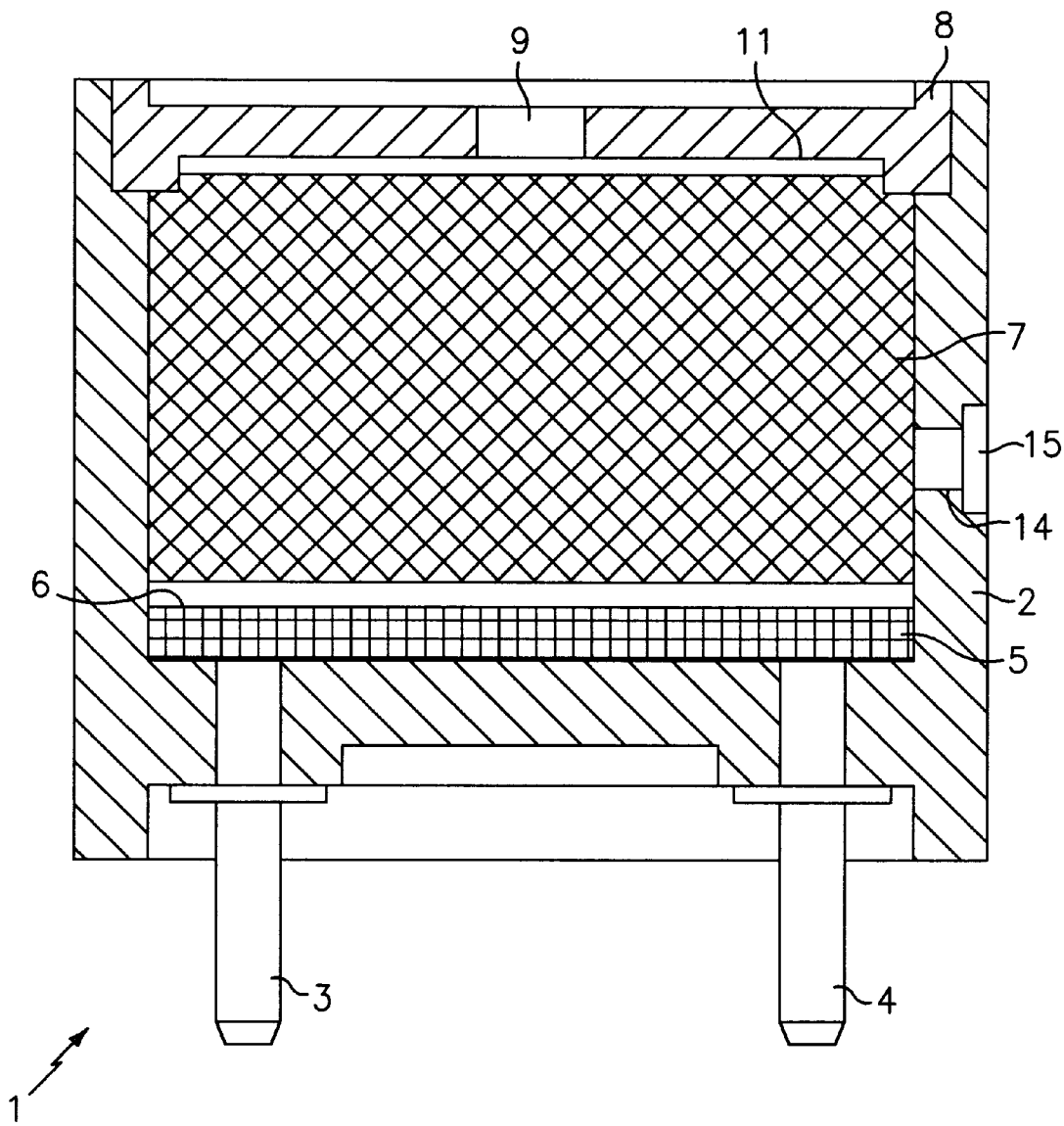
FIG. 1 is a sectional view of an electrochemical gas sensor.

Referring to FIG. 1, an electrochemical sensor 1 comprises a generally cylindrical cup 2 formed from plastics resin material. First and second contact pins 3, 4 extend through the base of the cup 2. A layer 5 of potting compound is located immediately over the floor of the cup 2. A first electrode structure 6 overlays the potting compound. A wad 7, comprising a roll of glass fibre textile, sits on top of the first electrode structure 6. The wad 7 is soaked in an electrolyte. A disc-shaped cap 8 is dimensioned to plug the open end of the cup 2. The cap 8 has an axial, centrally located hole 9 to allow gas to be sensed to pass into the cup 2. A first wire (not shown) extends from the first contact pin 3 and overlays the first electrode structure 6. A second wire (not shown) extends from the second contact pin 4, up the inside of the cup 2, and between the wad 7 and the second electrode structure 11 to provide a connection thereto.

An aperture 14 is provided in the side wall of the cup 2. This aperture 14 is stopped with a plug 15.

The first electrode 6 comprises a disc of gas-permeable PTFE, coated on one face with platinum black. The coated face forms an electrode and, in the assembled sensor 1, contacts the wad 7. The second electrode structure 11 has the same construction and its coated face is also in contact with the wad 7 in the assembled sensor 1.

The second electrode 11 allows the passage of gas. However, it prevents the electrolyte escaping through the hole 9 in the cap 8. The wad 7 acts as a wick to ensure that, whatever the orientation of the sensor, the electrode structures 6, 11 remain in contact with the electrolyte.

Figure 2:
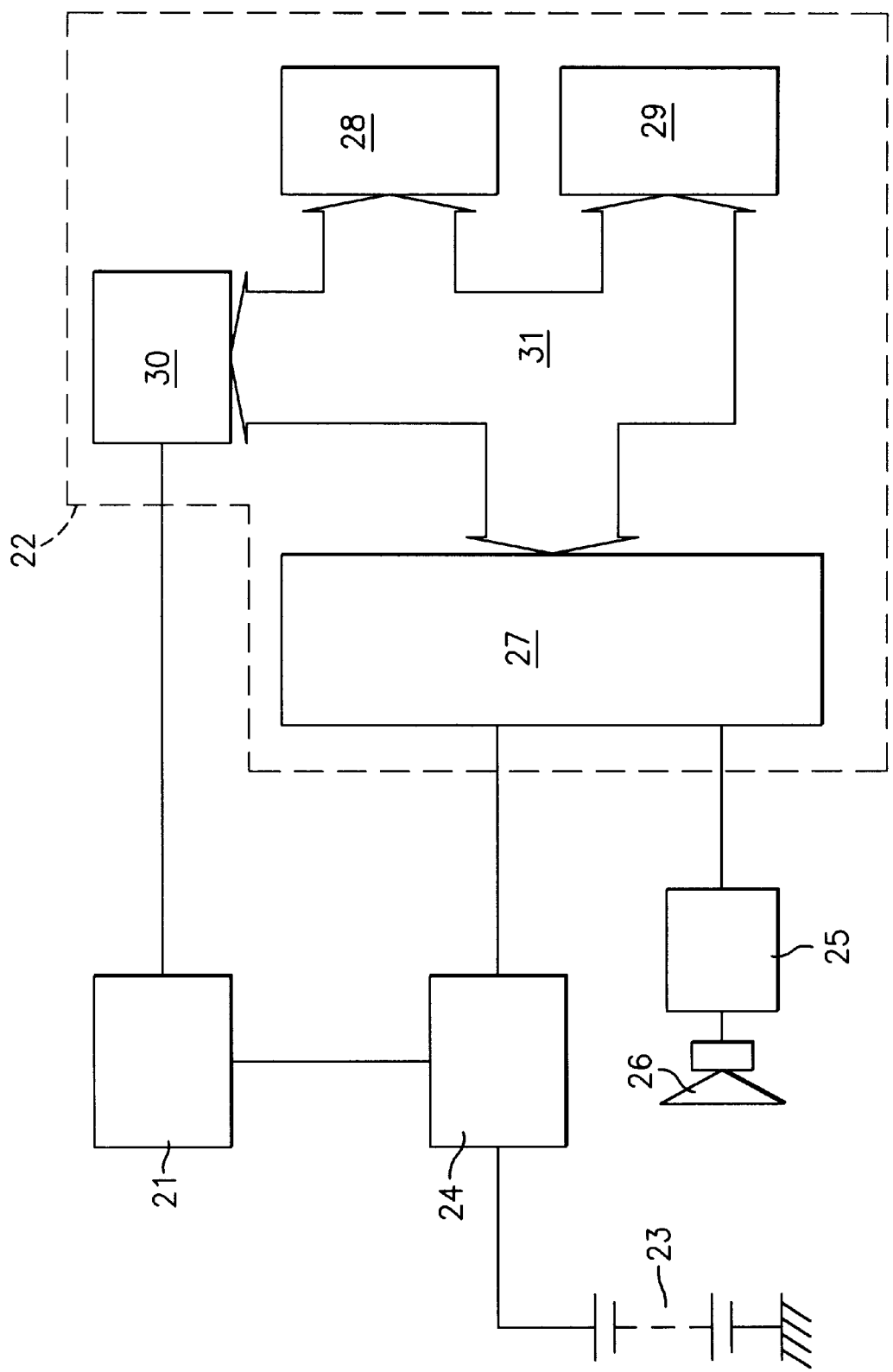
FIG. 2 s a block diagram of an apparatus according to the present invention.

Referring to FIG. 2, a gas detecting apparatus comprises a sensor circuit 21, a microcomputer 22 for analysing the output of the sensor circuit 21, a 3 V battery 23, a switching circuit 24 for selectively applying power to the sensor circuit 21 in dependence on a switching signal from the microcomputer 22, an alarm circuit 25 and a loudspeaker 26 connected to the alarm circuit 25.

The microcomputer 22 comprises a microprocessor 27, a read-only memory (ROM) 28 storing a control program, a random-access memory (RAM) 29 for storing data and an analogue-to-digital converter (ADC) 30. The components of the microcomputer 22 are connected by a data and address bus 31. The ADC 30 receives as its input the output of the sensor circuit 21. The microprocessor 27 is configured to have two 1-bit wide ports, the first of which is connected to the switching circuit 24 and the second of which is connected to the alarm circuit 25.

The microprocessor 27 is of a type (e.g. Motorola MC146805E2) which has a low-power consumption WAIT mode. CPU timer-generated interrupts are used to wake up the microprocessor 27 from its WAIT state.

Figure 3:
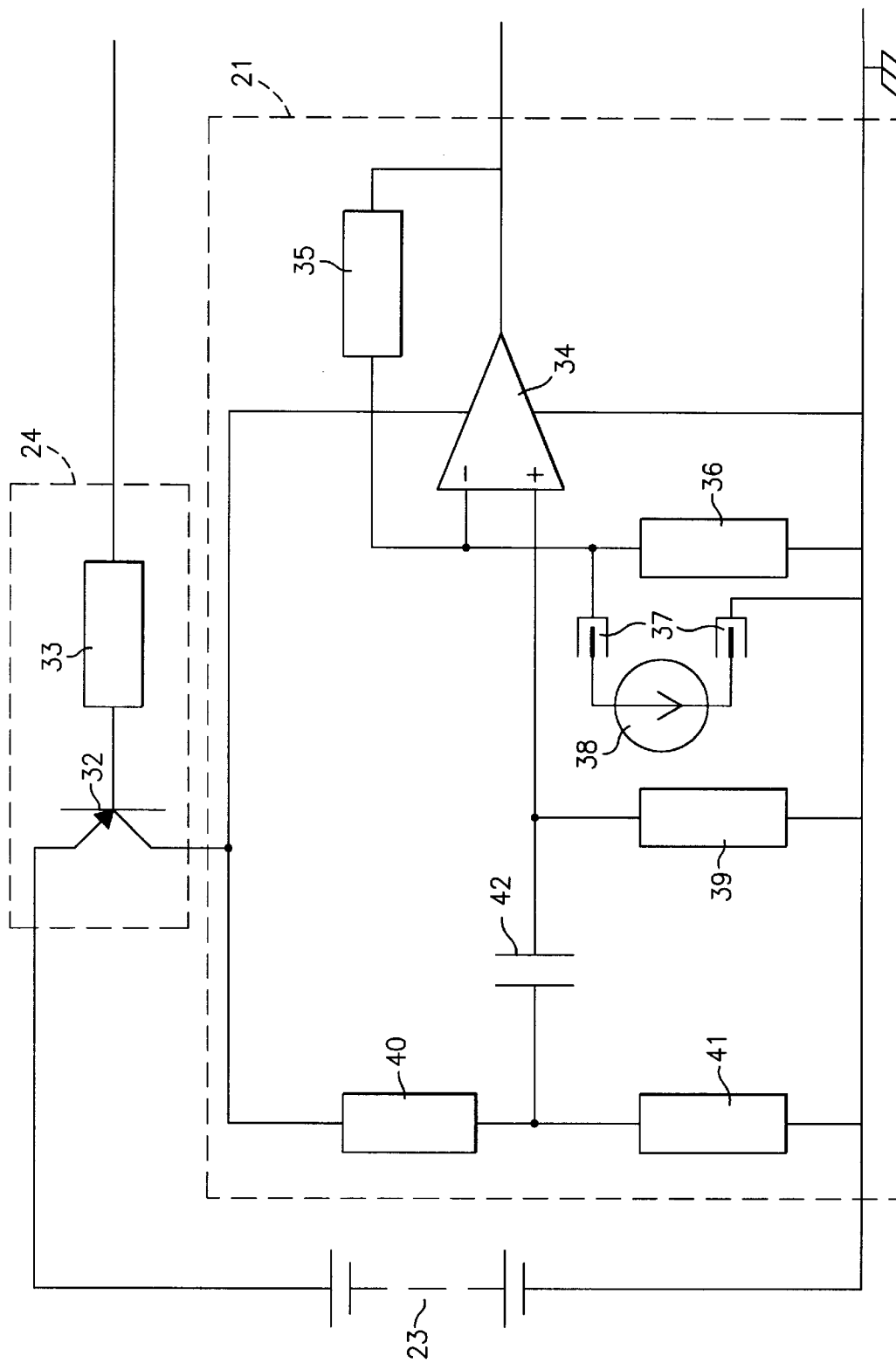
FIG. 3 is a circuit diagram of the amplifier circuit and the switching circuit of the apparatus of FIG. 2.

Referring to FIG. 3, the switching circuit 24 comprises a pnp switching transistor 32 and a resistor 33 connected between the base of the transistor 32 and the first 1-bit wide port of the microprocessor 27. The emitter of the transistor 32 is connected to the positive terminal of the battery 23.

The sensor circuit 21 includes an operational amplifier (op-amp) 34, a feedback resistor 35 connected between the output and the inverting input of the op-amp 34, a resistor 36 connected between the inverting input of the op-amp 34 and earth, a socket 37 for receiving a plug-in electrochemical gas sensor 38 and connecting it in parallel with resistor 36, a resistor 39 connected between the non-inverting input of the op-amp 34 and earth, a potential divider comprising two series-connected resistors 40, 41, and a capacitor 42 connecting the central node of the potential divider to the non-inverting input of the op-amp 34. One end of resistor 40 is connected to the collector of the switching transistor 32 and one end of resistor 41 is connected to earth. The positive supply terminal of the op-amp 34 is also connected to the collector of the switching transistor 32.

The operation of the gas detecting apparatus will now be described.

Figure 4:
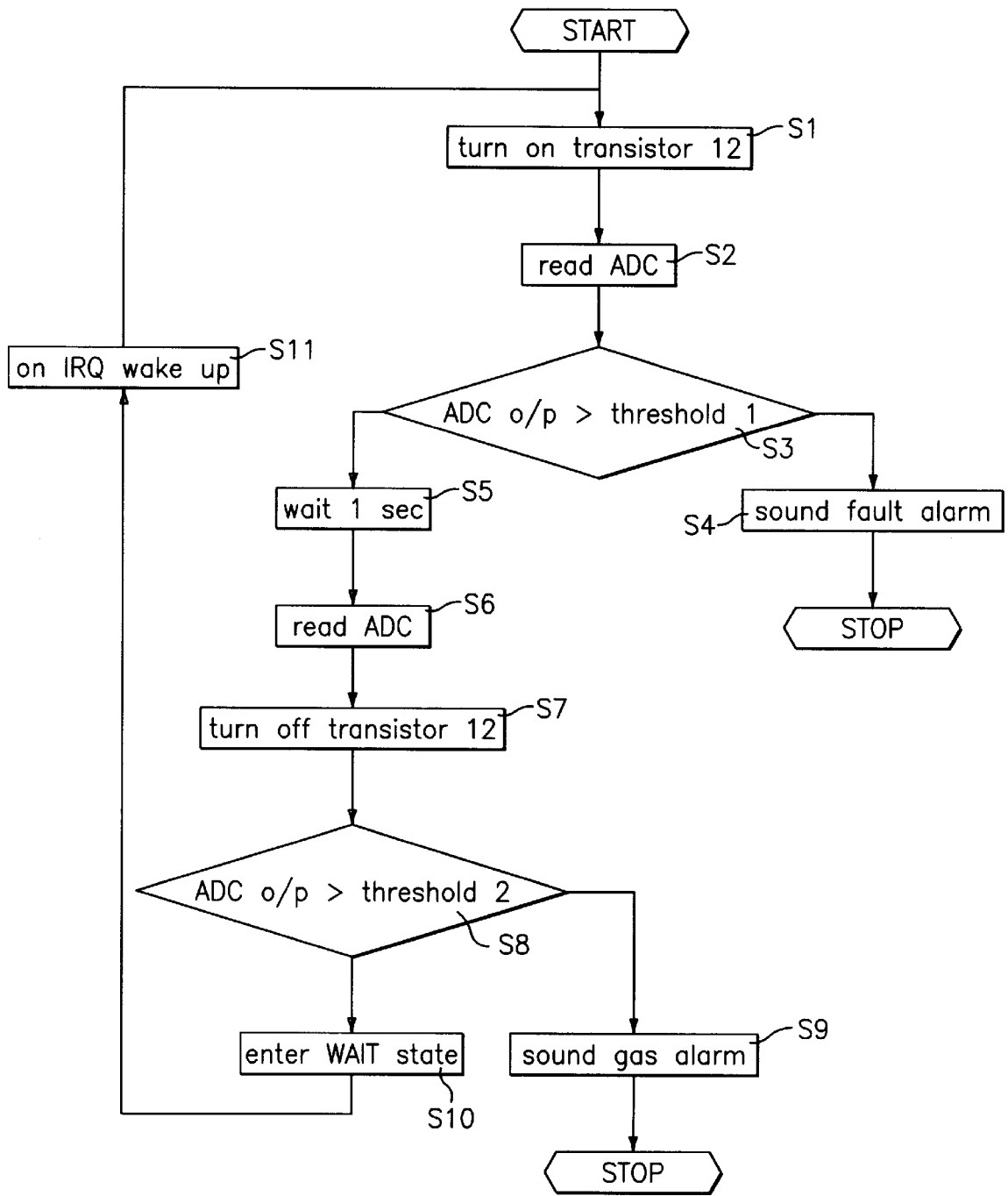
FIG. 4 is a flow chart illustrating the operation of the apparatus of FIG. 2.
Figure 5A:
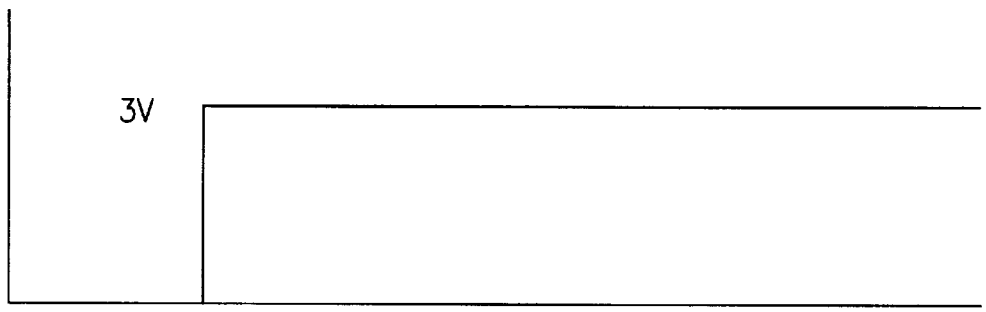
FIGS. 5(a)–5(d) are waveform diagrams illustrating the operation of the circuit of FIG. 3.
Figure 5B:
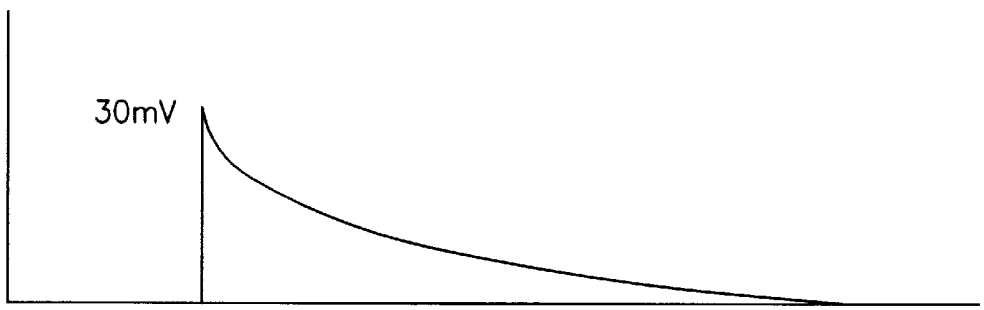

Referring to FIG. 4, when the microprocessor 27 becomes active, it outputs a 0 V signal from the first 1-bit wide port (step s1) to turn on the switching transistor 32. This applies power to the sensor circuit 21. The resistors 40, 41 of the potential divider have values in a ratio in the region of 99:1. Consequently, the voltage at the central node of the potential divider rises rapidly from 0 V to approximately 30 mV FIG. 5(a)) when the switching transistor 32 is turned on. This induces a corresponding voltage increase, the test signal, on the other side of the capacitor 42 across the resistor 39 (FIG. 5(b)). The voltage across the resistor 39 then decays exponentially. In other words, the capacitor 42 and the resistor 39 form an imperfect differentiator. The RC time constant of the resistor 40 and the capacitor 42 should be much less that that of the resistor 39 and the capacitor 42.

Figure 5C:
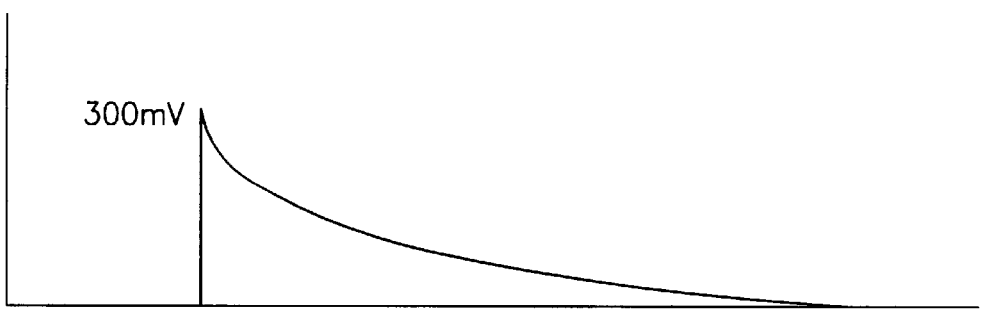

If no gas sensor 38 is plugged into the circuit, the gain of the op-amp 34 is determined by the ratio of the values of the resistor 35 and the resistor 36 (the well-known formula: $A_v = R_f/R_s$). This ratio is of the order of 10. Accordingly, the 30 mV peak signal across the resistor 39 will be amplified and output to the ADC 30 with a peak value of 300 mV (FIG. 5(c)).

At this point, the microprocessor 27 reads the ADC 30 (step s2). The value read from the ADC 30 is compared with a first threshold value, e.g. 1.5 V, (step s3). With no sensor 38 present, the value read from the ADC 30 will be below the first threshold and the microprocessor 27 then outputs a fault alarm signal to the alarm circuit 25 from the second 1-bit wide port (step s4). The fault alarm signal is normally at 0 V. However, in the event of a fault, the microprocessor 27 outputs pairs of pulses, the time between pairs being significantly greater that the time between the pulse of a pair. The alarm circuit 25 causes the loudspeaker 26 to output a tone pulse in response to each of the pulses from the microprocessor 27.

Figure 5D:
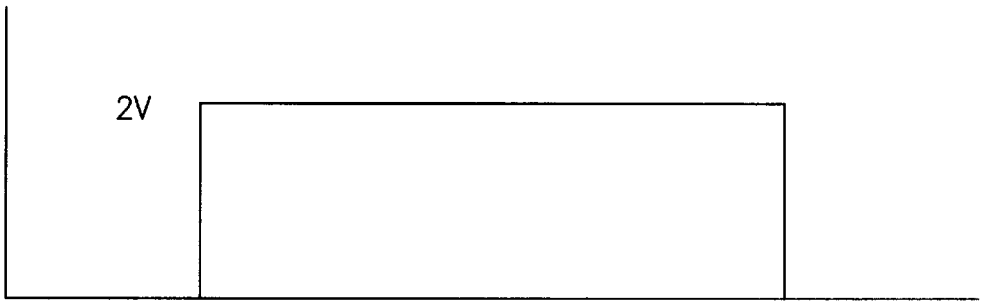

The sensor 38 has a large capacitance and consequently very low impedance for the frequency domain components of the transient, that is the test signal, appearing across the resistor 39. Consequently, the gain of the op-amp 34 is very high for the test signal. Indeed, the gain is so high that the op-amp's output saturates at, typically, 2 V from the start of the test signal until it has almost completely decayed away (FIG. 5(d)).

Thus, if a serviceable sensor 38 is present, the value read from the ADC at step s2 will be determined to be greater that the first threshold at step s3. In this case, the microprocessor 27 waits for 1 second (step s5), to allow the output of the op-amp 34 to fall from its saturation level, and then reads the ADC again (step s6). Once the ADC has been read for the second time, the sensor circuit 21 no longer needs to be active. Accordingly, the microprocessor 27 raises the output from its first 1-bit wide port to 3 V (step s7) to turn off the switching transistor 32.

The value read from the ADC at step s6, is then compared with a second threshold, representing a predetermined gas concentration (step s8). If the value is above the threshold, the microprocessor 27 sounds the gas alarm (step s9). The microprocessor 27 does this by outputting a series of equi-spaced 1-second pulses from the second 1-bit wide port. Corresponding tone pulses are then output by the loudspeaker 26.

If the second threshold has not been exceeded, the microprocessor 27 enters its dormant or WAIT state (step s10). The microprocessor 27 remains in this state until it is woken by an interrupt request generated by its CPU timer (step s11). Once, the microprocessor 27 has "woken up", it returns to step s1.

In the foregoing, the present invention has been described in the cases where a sensor is either present or absent. However, the present invention is also able to detect when a sensor is present but faulty. One of the failure modes of electrochemical sensors is a break in one of the wires leading to the electrodes. If this occurs, the capacitance of the sensor drops dramatically and the sensor appears as a simple open circuit. In this case, the sensor circuit 21 will behave as if no sensor were present.

Another failure mode of electrochemical sensors is the loss of electrolyte. If this occurs, the capacitance of the sensor 38 will fall, thereby reducing the gain of the op-amp 34 for the test signal. This will have the effect of shortening the length of the 2 V pulse output by the op-amp 34. A threshold corresponding to an acceptable amount of electrolyte can be set by introducing a delay between steps s1 and s2. In such an arrangement, the longer the delay, the smaller the amount of electrolyte that can be lost before the fault alarm is sounded.

The present invention has been described with reference to a gas alarm. However, it is equally applicable to a gas concentration monitoring and/or recording apparatus, in which the gas alarm function is optional. Apparatus according to the present invention may be connected to a central station by point-to-point links or over a network. In such systems, the fault and gas alarms would be notified to the central station. Neither of the alarm conditions need necessarily be indicated or sounded locally.

What is claimed is:

1. A self-testing gas detecting apparatus comprising an electrical interconnection for making a connection to an electrochemical gas sensor, a test signal generating circuit for generating a test signal which comprises a transient, an amplifier for processing the test signal from the test signal generating circuit according to a transfer function, and a signalling device, said interconnection being arranged for connecting an electrochemical gas sensor as a component of the amplifier so as to determine said transfer function, wherein the signalling device is responsive to the processed test signal output by the amplifier to signal a fault condition if the processed test signal is not indicative of a serviceable electrochemical gas sensor being connected into the amplifying circuit by said interconnection, and the amplifier comprises an operational amplifier, the interconnection is configured for connecting an electrochemical cell between the inverting input of the operational amplifier and ground, and the test signal generating circuit is configured to apply the test signal to the non-inverting input of the operational amplifier.

2. An apparatus according to claim 1, wherein said interconnection is configured such that the presence of a serviceable electrochemical sensor increases the gain of the amplifier for said test signal.

3. An apparatus according to claim 2, including a comparator for determining whether the amplifier output exceeds a predetermined threshold, wherein the test signal generating circuit is configured such that the test signal causes the amplifier output to exceed said predetermined threshold value when a serviceable electrochemical cell is connected to the amplifier by said interconnection.

4. An apparatus according to claim 3, including means to determine whether said predetermined threshold is exceeded for a predetermined period.

5. An apparatus according to claim 1, wherein the test signal generating circuit comprises means to produce a voltage step and a differentiator for differentiating the voltage step to produce the test signal.

6. An apparatus according to claim 5, wherein the means to produce a voltage step comprises a potential divider coupled between the amplifier's power supply lines.

7. An apparatus according to claim 6, including control means and switching means for switching the supply of power to the amplifier, wherein the control means is operable to operate the switching means to cyclically energise the amplifier.

8. A gas detecting apparatus comprising an electrical interconnection for receiving a two-terminal electrochemical gas sensor, a test signal generating circuit for generating a test signal which comprises a transient, an amplifier for processing the test signal from the test signal generating circuit and processing means responsive to the processed test signal output by the amplifier to determine whether a serviceable electrochemical gas sensor is connected to the interconnection, the interconnection being arranged for connecting an electrochemical gas sensor to the amplifier such that the transfer function of the amplifier for the test signal is influenced thereby, wherein the amplifier comprises an operational amplifier, the interconnection is configured for connecting an electrochemical cell between the inverting input of the operational amplifier and ground, and the test signal generating circuit is configured to apply the test signal to the non-inverting input of the operational amplifier.

9. An apparatus according to claim 8, wherein said interconnection is configured such that the presence of a serviceable electrochemical sensor increases the gain of the amplifier for said test signal.

10. An apparatus according to claim 9, including a comparator for determining whether the amplifier output exceeds a predetermined threshold, wherein the test signal generating circuit is configured such that the test signal causes the amplifier output to exceed said predetermined threshold value when a serviceable electrochemical cell is connected to the amplifier by said interconnection.

11. An apparatus according to claim 10, including means to determine whether said predetermined threshold is exceeded for a predetermined period.

12. An apparatus according to claim 8, wherein the test signal generating circuit comprises means to produce a voltage step and a differentiator for differentiating the voltage step to produce the test signal.

13. An apparatus according to claim 12, wherein the means to produce a voltage step comprises a potential divider coupled between the amplifier's power supply lines.

14. An apparatus according to claim 13, including control means and switching means for switching the supply of power to the amplifier, wherein the control means is operable to operate the switching means to cyclically energise the amplifier.

* * * * *